(12) United States Patent
Sayre et al.

(10) Patent No.: US 7,169,550 B2
(45) Date of Patent: Jan. 30, 2007

(54) DIFFRACTION-BASED DIAGNOSTIC DEVICES

(75) Inventors: Curtis Sayre, Atlanta, GA (US); Rosann Kaylor, Cumming, GA (US); David Cohen, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 688 days.

(21) Appl. No.: 10/256,278

(22) Filed: Sep. 26, 2002

(65) Prior Publication Data

US 2004/0063146 A1 Apr. 1, 2004

(51) Int. Cl.
*C12Q 1/00* (2006.01)

(52) U.S. Cl. .......................... 435/4; 422/82.11; 435/5; 435/6; 435/7.1; 435/7.2; 435/7.21; 435/7.22; 435/7.3; 435/7.31; 435/7.32; 435/7.34; 435/7.36; 435/7.37; 435/288.7; 436/513; 436/518; 436/524; 436/525; 436/527; 436/805; 436/815; 436/820; 436/901

(58) Field of Classification Search .................. None
See application file for complete search history.

(56) References Cited

U.S. PATENT DOCUMENTS

| | | |
|---|---|---|
| 3,641,354 A | 2/1972 | De Ment |
| 4,011,009 A | 3/1977 | Lama et al. |
| 4,274,706 A | 6/1981 | Tangonan |
| 4,312,228 A | 1/1982 | Wohltjen |
| 4,330,175 A | 5/1982 | Fujii et al. |
| 4,363,874 A | 12/1982 | Greenquist |
| 4,399,686 A | 8/1983 | Kindlund et al. |
| 4,416,505 A | 11/1983 | Dickson |
| 4,442,204 A | 4/1984 | Greenquist et al. |
| 4,477,158 A | 10/1984 | Pollock et al. |
| 4,480,042 A | 10/1984 | Craig et al. |
| 4,528,260 A | 7/1985 | Kane |
| 4,534,356 A | 8/1985 | Papadakis |
| 4,537,861 A | 8/1985 | Elings et al. |
| 4,552,458 A | 11/1985 | Lowne |
| 4,561,286 A | 12/1985 | Sekler et al. |
| 4,562,157 A | 12/1985 | Lowe et al. |
| 4,587,213 A | 5/1986 | Malecki |
| 4,596,697 A | 6/1986 | Ballato |
| 4,614,723 A | 9/1986 | Schmidt et al. |

(Continued)

FOREIGN PATENT DOCUMENTS

EP 0205698 A1 12/1986

(Continued)

OTHER PUBLICATIONS

Article—*A Fill-and-Flow Biosensor*, Gooding et al, Analytical Chemistry, vol. 70, No. 15, Aug. 1, 1999, pp. 3131-3136.

(Continued)

*Primary Examiner*—Christopher L. Chin
(74) *Attorney, Agent, or Firm*—Dority & Manning, P.A.

(57) ABSTRACT

A biosensor includes a substrate with a receptive material layer of radiation-absorbing member (RAM)-tagged biomolecules disposed thereon. The receptive material is specific for an analyte of interest. A pattern of active and deactivated areas of the receptive material are defined in the receptive material layer by a masking process wherein areas are exposed through a mask with a light source to induce deactivation.

14 Claims, 1 Drawing Sheet

U.S. PATENT DOCUMENTS

| | | |
|---|---|---|
| 4,632,559 A | 12/1986 | Brunsting |
| 4,647,544 A | 3/1987 | Nicoli et al. |
| 4,661,235 A | 4/1987 | Krull et al. |
| 4,690,715 A | 9/1987 | Allara et al. |
| 4,698,262 A | 10/1987 | Schwartz et al. |
| 4,776,944 A | 10/1988 | Janata et al. |
| 4,812,221 A | 3/1989 | Madou et al. |
| 4,815,843 A | 3/1989 | Tiefenthaler et al. |
| 4,818,710 A | 4/1989 | Sutherland et al. |
| 4,837,715 A | 6/1989 | Ungpiyakul et al. |
| 4,842,633 A | 6/1989 | Kuribayashi et al. |
| 4,842,783 A | 6/1989 | Blaylock |
| 4,844,613 A | 7/1989 | Batchelder et al. |
| 4,851,816 A | 7/1989 | Macias et al. |
| 4,876,208 A | 10/1989 | Gustafson et al. |
| 4,877,747 A | 10/1989 | Stewart |
| 4,882,288 A | 11/1989 | North et al. |
| 4,895,017 A | 1/1990 | Pyke et al. |
| 4,917,503 A | 4/1990 | Bhattacharjee |
| 4,931,384 A | 6/1990 | Layton et al. |
| 4,992,385 A | 2/1991 | Godfrey |
| 4,999,489 A | 3/1991 | Huggins |
| RE33,581 E | 4/1991 | Nicoli et al. |
| 5,023,053 A | 6/1991 | Finlan |
| 5,035,863 A | 7/1991 | Finlan et al. |
| 5,055,265 A | 10/1991 | Finlan |
| 5,057,560 A | 10/1991 | Mueller |
| 5,063,081 A | 11/1991 | Cozzette et al. |
| 5,064,619 A | 11/1991 | Finlan |
| 5,071,248 A | 12/1991 | Tiefenthaler et al. |
| 5,076,094 A | 12/1991 | Frye et al. |
| 5,089,387 A | 2/1992 | Tsay et al. |
| 5,096,671 A | 3/1992 | Kane et al. |
| 5,114,676 A | 5/1992 | Leiner et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,152,758 A | 10/1992 | Kaetsu et al. |
| 5,155,791 A | 10/1992 | Hsiung |
| 5,182,135 A | 1/1993 | Giesecke et al. |
| 5,189,902 A | 3/1993 | Groeninger |
| 5,196,350 A | 3/1993 | Backman et al. |
| 5,225,935 A | 7/1993 | Watanabe et al. |
| 5,235,238 A | 8/1993 | Nomura et al. |
| 5,238,815 A | 8/1993 | Higo et al. |
| 5,242,828 A | 9/1993 | Bergstrom et al. |
| 5,262,299 A | 11/1993 | Evangelista et al. |
| 5,268,306 A | 12/1993 | Berger et al. |
| 5,280,548 A | 1/1994 | Atwater et al. |
| 5,304,293 A | 4/1994 | Tierney et al. |
| 5,310,686 A | 5/1994 | Sawyers et al. |
| 5,315,436 A | 5/1994 | Lowenhar et al. |
| 5,321,492 A | 6/1994 | Detwiler et al. |
| 5,327,225 A | 7/1994 | Bender et al. |
| 5,334,303 A | 8/1994 | Muramatsu et al. |
| 5,352,582 A | 10/1994 | Lichtenwalter et al. |
| 5,369,717 A | 11/1994 | Attridge |
| 5,374,563 A | 12/1994 | Maule |
| 5,376,255 A | 12/1994 | Gumbrecht et al. |
| 5,378,638 A | 1/1995 | Deeg et al. |
| 5,389,534 A | 2/1995 | von Gentzkow et al. |
| 5,402,075 A | 3/1995 | Lu et al. |
| 5,404,756 A | 4/1995 | Briggs et al. |
| 5,415,842 A | 5/1995 | Maule |
| 5,418,136 A | 5/1995 | Miller et al. |
| 5,424,220 A | 6/1995 | Goerlach-Graw et al. |
| 5,430,815 A | 7/1995 | Shen et al. |
| 5,436,161 A | 7/1995 | Bergstrom et al. |
| 5,451,683 A | 9/1995 | Barrett et al. |
| 5,455,178 A | 10/1995 | Fattinger |
| 5,455,475 A | 10/1995 | Josse et al. |
| 5,464,741 A | 11/1995 | Hendrix |
| 5,468,606 A | 11/1995 | Bogart et al. |
| 5,478,527 A | 12/1995 | Gustafson et al. |
| 5,482,830 A | 1/1996 | Bogart et al. |
| 5,482,867 A | 1/1996 | Barrett et al. |
| 5,489,678 A | 2/1996 | Fodor et al. |
| 5,489,988 A | 2/1996 | Ackley et al. |
| 5,492,840 A | 2/1996 | Malmqvist et al. |
| 5,496,701 A | 3/1996 | Pollard-Knight |
| 5,510,481 A | 4/1996 | Bednarski et al. |
| 5,510,628 A | 4/1996 | Georger, Jr. et al. |
| 5,512,131 A | 4/1996 | Kumar et al. |
| 5,514,501 A | 5/1996 | Tarlov |
| 5,514,559 A | 5/1996 | Markert-Hahn et al. |
| 5,516,635 A | 5/1996 | Ekins et al. |
| 5,518,689 A | 5/1996 | Dosmann et al. |
| 5,527,711 A | 6/1996 | Tom-Moy et al. |
| 5,552,272 A | 9/1996 | Bogart |
| 5,554,541 A | 9/1996 | Malmqvist et al. |
| 5,569,608 A | 10/1996 | Sommer |
| 5,573,909 A | 11/1996 | Singer et al. |
| 5,580,697 A | 12/1996 | Keana et al. |
| 5,580,921 A | 12/1996 | Stepp et al. |
| 5,585,279 A | 12/1996 | Davidson |
| 5,589,401 A | 12/1996 | Hansen et al. |
| 5,591,581 A | 1/1997 | Massey et al. |
| 5,599,668 A | 2/1997 | Stimpson et al. |
| 5,620,850 A | 4/1997 | Bamdad et al. |
| 5,637,509 A | 6/1997 | Hemmilä et al. |
| 5,643,681 A | 7/1997 | Voorhees et al. |
| 5,658,443 A | 8/1997 | Yamamoto et al. |
| 5,677,196 A | 10/1997 | Herron et al. |
| 5,731,147 A | 3/1998 | Bard et al. |
| 5,780,251 A | 7/1998 | Klainer et al. |
| 5,811,526 A | 9/1998 | Davidson |
| 5,814,565 A | 9/1998 | Reichert et al. |
| 5,827,748 A | 10/1998 | Golden |
| 5,830,762 A | 11/1998 | Weindel |
| 5,832,165 A | 11/1998 | Reichert et al. |
| 5,843,692 A | 12/1998 | Phillips et al. |
| 5,863,740 A | 1/1999 | Kientsch-Engel et al. |
| 5,910,940 A | 6/1999 | Guerra |
| 5,922,537 A | 7/1999 | Ewart et al. |
| 5,922,550 A | 7/1999 | Everhart et al. |
| 5,922,615 A | 7/1999 | Nowakowski et al. |
| 5,965,305 A | 10/1999 | Ligler et al. |
| 6,030,840 A | 2/2000 | Mullinax et al. |
| 6,048,623 A | 4/2000 | Everhart et al. |
| 6,060,237 A | 5/2000 | Nygren et al. |
| 6,060,256 A | 5/2000 | Everhart et al. |
| 6,084,683 A | 7/2000 | Bruno et al. |
| 6,107,038 A | 8/2000 | Choudhary et al. |
| 6,113,855 A | 9/2000 | Buechler |
| 6,136,611 A | 10/2000 | Saaski et al. |
| 6,171,780 B1 | 1/2001 | Pham et al. |
| 6,180,288 B1 | 1/2001 | Everhart et al. |
| 6,182,571 B1 | 2/2001 | Jolliffe et al. |
| 6,200,820 B1 | 3/2001 | Hansen et al. |
| 6,203,758 B1 | 3/2001 | Marks et al. |
| 6,221,579 B1 | 4/2001 | Everhart et al. |
| 6,287,783 B1 | 9/2001 | Maynard et al. |
| 6,287,871 B1 | 9/2001 | Herron et al. |
| 6,297,060 B1 | 10/2001 | Nowakowski et al. |
| 6,312,961 B1 | 11/2001 | Voirin et al. |
| 6,331,438 B1 | 12/2001 | Aylott et al. |
| 6,362,011 B1 | 3/2002 | Massey et al. |
| 6,395,558 B1 | 5/2002 | Duveneck et al. |
| 6,399,295 B1 | 6/2002 | Kaylor et al. |
| 6,399,397 B1 | 6/2002 | Zarling et al. |
| 6,411,439 B2 | 6/2002 | Nishikawa |
| 6,416,952 B1 | 7/2002 | Pirrung et al. |
| 6,423,465 B1 | 7/2002 | Hawker et al. |

| | | | |
|---|---|---|---|
| 6,436,651 | B1 | 8/2002 | Everhart et al. |
| 6,448,091 | B1 | 9/2002 | Massey et al. |
| 6,455,861 | B1 | 9/2002 | Hoyt |
| 6,468,741 | B1 | 10/2002 | Massey et al. |
| 6,556,299 | B1 | 4/2003 | Rushbrooke et al. |
| 6,573,040 | B2 | 6/2003 | Everhart et al. |
| 6,579,673 | B2 | 6/2003 | McGrath et al. |
| 6,582,930 | B1 | 6/2003 | Ponomarev et al. |
| 6,613,583 | B1 | 9/2003 | Richter et al. |
| 6,653,151 | B2 | 11/2003 | Anderson et al. |
| 6,743,581 | B1 | 6/2004 | Vo-Dinh |
| 6,790,531 | B2 | 9/2004 | Fournier |
| 2002/0028455 | A1 | 3/2002 | Laibinis et al. |
| 2003/0027327 | A1 | 2/2003 | Cunningham et al. |
| 2004/0058385 | A1 | 3/2004 | Abel et al. |

FOREIGN PATENT DOCUMENTS

| | | |
|---|---|---|
| EP | 0420053 A1 | 4/1991 |
| EP | 0453820 A2 | 10/1991 |
| EP | 0453820 A3 | 10/1991 |
| EP | 0453820 B1 | 10/1991 |
| EP | 0539035 A2 | 4/1993 |
| EP | 0539035 B1 | 4/1993 |
| EP | 0596421 A1 | 5/1994 |
| EP | 0657737 A2 | 6/1995 |
| EP | 0657737 A3 | 6/1995 |
| EP | 1566627 A1 | 8/2005 |
| GB | 2273772 | 6/1994 |
| WO | 9005305 | 5/1990 |
| WO | 9105999 | 5/1991 |
| WO | WO 9113998 A1 | 9/1991 |
| WO | 9403496 | 2/1994 |
| WO | WO 9413835 A1 | 6/1994 |
| WO | 9415193 | 7/1994 |
| WO | WO 9609532 A1 | 3/1996 |
| WO | 9615193 | 5/1996 |
| WO | WO 9612962 A1 | 5/1996 |
| WO | 9626435 | 8/1996 |
| WO | WO 9624062 A1 | 8/1996 |
| WO | 9629629 | 9/1996 |
| WO | 9633971 | 10/1996 |
| WO | WO 9301308 A1 | 1/1998 |
| WO | 9810334 | 3/1998 |
| WO | WO 9815831 A1 | 4/1998 |
| WO | 9827417 | 6/1998 |
| WO | WO 9910742 A1 | 3/1999 |
| WO | WO 9930131 A1 | 6/1999 |
| WO | WO 9931486 A1 | 6/1999 |
| WO | WO 0050891 A1 | 8/2000 |
| WO | WO 0171322 A2 | 9/2001 |
| WO | WO 0181921 A2 | 11/2001 |
| WO | WO 0181921 A3 | 11/2001 |

OTHER PUBLICATIONS

Article—*Diffraction-Based Cell Detection Using a Microcontact Printed Antibody Grating*, St. John et al., Analytical Chemistry, vol. 70, No. 6, Mar. 15, 1998, pp. 1108-1111.
Article—*Micro-Scale Patterning of Biological Molecules*, Pritchard et al., Angew. Chem. Int. Ed. Engl., vol. 34, No. 1, 1995, pp. 91-93.
Article—*Oxidation of Self-Assembled Monolayers by UV Light with a Wavelength of 254 nm*, Brewer et al., J. Am. Chem. Soc., vol. 123, 2001, pp. 4089-4090.
Abstract of Japanese Patent No. JP2085755, Mar. 27, 1990.
Abstract of Japanese Patent No. JP2140702, May. 20, 1990.
Abstract of Japanese Patent No. JP2165933, Jun. 26, 1990.
Abstract of Japanese Patent No. JP2210302, Aug. 21, 1990.
Abstract of Japanese Patent No. JP5132640, May. 28, 1993.
Abstract of Japanese Patent No. JP8062214, Mar. 8, 1996.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70. No. 3, Feb. 1, 1998, pp. 596-601.

Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*How to Build a Spectrofluorometer*, Spex Fluorolog 3, Horiba Group, pp. 1-14.
Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phorphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, 2001, pp. 883-889.
Article—*Latex Immunoassays*, Leigh B. Bangs, Journal of Clinical Immunoassay, vol. 13, No. 3, 1990, pp. 127-131.
Article—*Longwave luminescent porphyrin probes*, Dmitry B. Papkovsky, Gelii V. Ponomarev, and Otto S. Wolfbeis, Spectrochimica Acta Part A, vol. 52, 1996, pp. 1629-1638.
Article—*Monofunctional Derivatives of Coproporphyrins for Phosphorescent Labeling of Proteins and Binding Assays*, Analystical Biochemistry, vol. 290, 2001, pp. 366-375.
Article—*Near Infrared Phosphorescent Metalloporphyrins*, Alexander P. Savitsky, Anna V. Savitskaja, Eugeny A. Lukjanetz, Svetlana N. Dashkevich, and Elena A. Makarova, SPIE, vol. 2980, pp. 352-357.
Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.
Article—*Performance Evaluation of the Phosphorescent Porphyrin Label: Solid-Phase Immunoassay of a-Fetoprotein*, Tomás C. O'Riordan, Aleksi E. Soini, Juhani T. Soini, and Dmitri B. Papkovsky, Analytical Chemistry, Vo. 74, No. 22, Nov. 15, 2002, pp. 5845-5850.
Article—*Phosphorescent porphyrin probes in biosensors and sensitive bioassays*, D. B. Papkovsky, T. O'Riordan, and A. Soini, Biochemical Society Transactions, vol. 28, Part 2, 2000, pp. 74-77.
Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.
Article—*Room-Temperature Phosphorescent Palladium-Porphine Probe for DNA Dtermination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.
*Fluorescent Microsphere Standards for Flow Cytometry and Fluorescence Microscopy* from Molecular Probes, pp. 1-8.
*FluoSpheres® Fluorescent Microspheres*, Product Information from Molecular Probes, Mar. 13, 2001, pp. 1-6.
*Magnetic Microparticles*, Polysciences, Inc. Techical Data Sheet 438, 2 pages.
*Working With FluoSpheres® Fluorescent Microspheres*, Properties and Modifications, Product Information from Molecular Probes, Mar. 9, 2001, pp. 1-5.
PCT Search Report for PCT/US03/11757, filed May 4, 2004.
PCT Search Report for PCT/US03/11757, filed May 6, 2004.
PCT Search Report for PCT/US03/29005, filed Feb. 12, 2004.
U.S. Appl. No. 10/180,219, Filed Jun. 26, 2002.
Letter to the Editors, Comment on the Prediction of Segregation to Alloy Surfaces, Copyright-1977.
Prediction of Segregation to Alloy Surfaces from Bulk Phase Diagrams, Physical Review Letters, vol. 37, No. 21, Nov. 22, 1976.
Orientation Dependence of Surface Segregation in a Dilute Ni-Au Alloy, Research Staff, Ford Motor Company, Dearborn, MI, Received Sep. 19, 1977; Accepted Nov. 18, 1977.

Volume Phase Transition of N-Alkylacrylamide Gels, Department of Molecular Chemistry and Engineering, Tohoku University, Advances on Polymer Science vol. 109, 1993.
Molecular Design of Temperature-Responsive Polymers as Intelligent Materials, Institute of Biomedical Engineering, Tokyo Women's Medical College, Advances on Polymer Science, vol. 110.
Molecular Gradients of w-Substituted Alkanethiols on Gold: Preparation and Characterization, Laboratory of Applied Physics, 1995 American Chemical Society, Jun. 6, 1995.
Acoustic Plate Waves for Measurements of Electrical Properties of Liquids, Microchemical Journal 43, 155-164, Jan. 31, 1991.
Analysis of Electrical Equivalent Circuit of Quartz Crystal Resonator Loaded with Viscous Conductive Liquids, Journal of Electroanalytical Chemistry 379 (1994) 21-33, Apr. 12, 1994.
Quartz Crystal Resonators as Sensors in Liquids Using the Acoustoelectric Effect, Anal. Chem. 1994, 66, 1955-1964.
Features of Gold Having Micrometer to Centimeter Dimensions can be Formed Through a Combination of Stamping with an Elastomeric Stamp and an Alkanethiol "Ink" Following by Chemical Etching, Appl. Phys. Lett. 63 (14), Oct. 4, 1993.
Photolithography of Self-Assembled Monolayers: Optimization of Protecting Roups by an Electroanalytical Method, Can. J. Chem. 74; 2509-2517 (1996).
Order in Microcontact Printed Self-Assembled Monolayers, Contributions of the IBM Research division, Nov. 26, 1996.
Combining Patterned Self-Assembled Monolayers of Alkanethiolates on Gold with Anisotropic Etching of Silicon to Generate Controlled Surface Morphologies, J. Electrochem. Soc., vol. 142, No. 2, Feb. 1995.
109 Advances in Polymer Science, Responsive Gels: Volume Transitions I, Springer Verlag Berlin Heidelberg 1993.
110 Advances in Polymer Science, Responsive Gels: Volume Transitions II, Springer Verlag Berlin Heidelberg 1993.
Intelligent Gels, Scientific American May 1993.
Volume Phase Transition and Related Phenomena of Polymer Gels, Advances in Polymer Science, vol. 109, Springer-Verlag Berlin Heidelberg 1993.
Novel Applications for Stimulus-Sensitive Polymer Gels in the Preparation of Functional Immobilized Biocatalysts, Advances in Polymer Science, vol. 110, Verlag Berlin Heidelberg 1993.
Stimuli-Responsive Polymer Gels and Their Application to Chemomechanical Systems, Prg. Polym. Sci. vol. 18, 187-226, 1993.
Electrical Surface Perturbation of a Piezoelectric Acoustic Plate Mode by a Conductive Liquid Loading, IEEE Transactions on Ulstrasonics, Ferroelectrics, and Frequency Control, vol. 39, No. 4, Jul. 1992.
On the Use of ZX-LiNbO$_3$ Acoustic Plate Mode Devices as Detectors for Dilute Electrolytes, Sensors and Actuators B.9 (1992) 97-112.
Probing of Strong and Weak Electrolytes with Acoustic Wave Fields, Sensors and Actuators B.9 (1992) 155-162.
Using Micromachining, Molecular Self-Assembly, and Wet Etching to Fabricate 0.1-1 um Scale Structures of Gold and Silicon, Chemistry of Materials, 1994.
Patterned Self-Assembled Monolayers Formed by Microcontact Printing Direct Selective Metalization by Chemical Vapor Deposition on Planar and Nonplanar Substrates, Langmuir 1995, 11, 3024-3026.
Self-Assembled Monolayers of Long-Chain Hydroxamic ACIS on the Native Oxides of Metals, Langmuir, 1995, 11.
Microfabrication by Microcontact Printing of Self-Assembled Monolayers, VCH Verlagsgesellschaf T mbH 1884.
Patterned Condensation Figures as Optical Diffraction Gratings, American Association for the Advancement of Science, 1994.
Stimuli-Responsive Poly (N-Isoproplylacrylamide). Photo- and Chemical-Induced Phase Transitions, Advances in Polymer Science No. 110, 1993.
Quantitative Prediction of Surface Segregation, Journal of Catalysis 57, 450-457 (1970).
Sensing Liquid Properties with Thickness-Shear Mode Resonators, Sensors and Actuators A 44 (1994) 209-218.

Direct Observation of Streptavidin Specifically Adsorbed on Biotin-Functionalized Self-Assembled Monolayers wih the Scanning Tunneling Microscope, Angew Chem. Int. Ed. Engl. 30 (1991) No. 5.
New Approach to Producing Patterned Biomolecular Assemblies, Journal of the American Chemical Society, 1992.
The Biotin-(Strept) Avidin System: Principles and Applications in Biotechnology, Clinical Chemistry, vol. 37, No. 5, 1991.
Fabrication of Surfaces Resistant to Protein Adsorption and Application to Two-Dimensional Protein Patterning, Analytical Biochemistry 208, 197-205 (1993).
Patterning Self-Assembled Monolayers Using Microcontact Printing: A New Technology for Biosensors?, Department of Chemistry, Harvard University.
Photosensitve Self-Assembled Monolayers on Gold: Photochemistry of Surface-Confined Aryl Azide and Cyclopentadienylmanganese Tricarbonyl, American Chemical Society, 1994.
Generation of Electrochemically Deposited Metal Patterns by Means of Electron Beam (Nano)Lithography of Self-Assembled Monolayer Resists, American Institute of Physics, 1994.
Selective Electrochemical Deposition of Polyaniline Via Photopatterning of a Monolayer-Modified Substrate, American Chemical Society 1994.
Pattern Transfer of Electron Beam Modified Self-Assembled Monolayers for High-Resolution Lithography, J. Vac. Sci. Technol. B 13(3) May/Jun. 1995.
Patterned Functionalization of Gold and Single Crystal Silicon Via Photochemical Reaction of Surface-Confined Derivatives of ($N^5$-$C_5H_5$)Mn(CO)$_3$, American Chemical Society 1991.
Photopatterning aned Selective Electroless Metallization of Surface-Attached Ligands, American Chemical Society 1993.
Control of the Shape of Liquid Lenses on a Modified Gold Surface Using an Applied Electrical Potential Across a Self-Assembled Monolayer, American Chemical Society, 1995.
Fabrication of Patterned, Electrically Conducting Polypyrrole Using a Self-Assembled Monolayer: A Route to All-Organic Circuits, American Chemical Society 1995.
Wet Chemical Approaches to the Characterization of Organic Surfaces: Self-Assembled Monolayers, Wetting, and the Physical-Organic Chemistry of the Solid-Liquid Chemistry of the Solid-Liquid Interface, Department of Chemistry, Harvard University, 1989.
UV Photpatterning of Alkanethiolate Monolayers Self-Assembled on Gold and Silver, American Chemical Society 1993.
The Use of Self-Assembled Monolayers and a Selective Etch to Generate Patterned Gold Features, American Checmial Society 1992.
Use of a Patterned Self-Assembled Monolayer to Control the Formation of a Liquid Resist Pattern on a Gold Surface, American Chemical Society 1995.
Self-Organization of Organic Liquids on Patterned Self-Assembled Monolayers of Alkanethiolates on Gold, Langmuir 1994.
Self-Assembled Monlayer Electron Beam Resist on GaAS, American Institute of Physics 1993.
Manipulation of the Wettability of Surfaces on the 0.1- to 1-Micrometer Scale Through Micromachining and Molecular Self-Assembly, Science, vol. 257, Sep. 1992.
Comparison of the Structures and Wetting Properties of Self-Assembled Monolayers of n-Alkanethiols on the Coinage Metal Surfaces, Cu, Ag, Au, American Chemical Society, 1991.
Self-Assembled Monolayer Films for Nanofabrication, Mat. Res. Soc. Symp. Proc. vol. 380, 1995 Materials Research Society.
Patterned Metal Electrodeposition Using an Alkanethiolate Mask, J. Electrochem. Soc. vol. 142, No. 11, Nov. 1995.
Biospecific Adsorption of Carbonic Anhydrase to Self-Assembled Monolayers of Alkanethiolates that Present Benzenesulfonamide Groups on Gold, American Chemical Society, 1995.
Microcontact Printing of Octadecylsiloxane on the Surface of Silicon Dioxide and Its Application in Microfabrication, American Chemical Society 1995.
Attempts to Mimic Docking Processes of the Immune System: Recognition-Induced Formation of Protein Multilayer, Science, vol. 262, Dec. 10, 1993.

Mechanical Resonance Gas Sensors with Piezoelectric Excitation and Detection Using PVDF Polymer Foils, Elsevier Sequoia 1992.

Application of Rod-Like Polymers with Ionophores as Langmuir-Blodgett Membranes for Si-Based Ion Sensors, Elsevier Sequoia 1992.

Patterning Self-Assembled Monolayers: Applications in Materials Science, Department of Chemistry, Harvard University, Feb. 18, 1994.

Optical Biosensor Assay (OBA), Clincal Chemistry, vol. 37, No. 9, 1991.

Laser-Mediated Protein Inactivation for Taget Validation, Jul./Aug. 2001.

Chromophore-Assisted Laser Inactivation of Proteins is Mediated by the Photogeneration of Free Radicals, Proc. Natl. Acad. Sci. USA, vol. 91, pp. 2659-2663, Mar. 1994, Biophysics.

Introduction to Flourescence Techniques, Molecular Probes, Inc. Copyright 1996-2002.

DIFFRACTION-BASED DIAGNOSTIC DEVICES

TECHNICAL FIELD OF THE INVENTION

The present invention relates generally to the field of detecting analytes in a medium, and more particularly to a process for preparing analyte-specific diffraction based diagnostic sensors to indicate the presence of the analyte in a medium.

BACKGROUND

There are many systems and devices available for detecting a wide variety of analytes in various media. Many of the prior systems and devices are, however, relatively expensive and require a trained technician to perform the test. A need has been recognized in the art for biosensor systems that are easy and inexpensive to manufacture, and capable of reliable and sensitive detection of analytes. Reference is made, for example, to U.S. Pat. Nos. 5,922,550; 6,060,256; and 6,221,579 B1.

U.S. Pat. No. 5,512,131 to Kumar, et al., describes a device that includes a polymer substrate having a metal coating. An analyte specific receptor layer is stamped onto the coated substrate. A diffraction pattern is generated when an analyte binds to the device. A visualization device is then used to determine the presence of the diffraction pattern. A drawback to this type of device is, however, the fact that the diffraction pattern is not discernible by the naked eye and, thus, a complex visualization device is needed to view the diffraction pattern. Also, the device is generally not able to detect smaller analytes that do not produce a noticeable diffraction pattern.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color. The second color is exhibited in response to the same light when the analyte is present on the surface. The change from one color to another can be measured either by use of an instrument, or by the naked eye. Drawbacks of this device are the relatively high cost of the device, problems associated with controlling the various layers that are placed on the surface, and the high variability of human color perception and discrimination.

Contact printing techniques have been explored for producing biosensors having a self-assembling monolayer. U.S. Pat. No. 5,922,550 describes a biosensor having a metalized film upon which is printed (contact printed) a specific predetermined pattern of an analyte-specific receptor. The receptor materials are bound to the self-assembling monolayer and are specific for a particular analyte or class of analytes. Attachment of a target analyte that is capable of scattering light to select areas of the metalized plastic film upon which the receptor is printed causes diffraction of transmitted and/or reflected light. A diffraction image is produced that can be easily seen with the eye or, optionally, with a sensing device.

U.S. Pat. No. 6,060,256 describes a similar device having a metalized film upon which is printed a specific predetermined pattern of analyte-specific receptor. The '256 patent is not limited to self-assembling monolayers, but teaches that any receptor which can be coupled to a surface can be used. The invention of the '256 patent uses contact printing methods to pattern monolayers using derivatives of binders for microorganisms. One example of such a derivative is a thiol. The desired binding agent can be thiolated antibodies or antibody fragments, proteins, nucleic acids, sugars, carbohydrates, or any other functionality capable of binding an analyte. The derivatives are chemically bonded to metal surfaces such as metalized polymer films, for example via a thiol.

The present invention relates to a biosensor system that is easy and inexpensive to manufacture, is capable of reliable and sensitive detection of analytes, and avoids possible drawbacks of conventional microcontact printing techniques.

SUMMARY OF THE INVENTION

Objects and advantages of the invention will be set forth in part in the following description, or may be obvious from the description, or may be learned through practice of the invention.

The present invention provides a relatively inexpensive yet sensitive biosensor device, a method for producing such biosensor devices, and a method for detecting analytes of interest present in a medium.

The biosensor includes a substrate upon which a layer containing a receptive material (e.g., biomolecules) has been applied generally uniformly over the entire surface of the substrate. The substrate may be any one of a wide variety of suitable materials, including plastics, metal coated plastics and glass, functionalized plastics and glass, silicon wafers, foils, glass, etc. Desirably, the substrate is flexible, such as a polymeric film, to facilitate the manufacturing process. The receptive material layer may be applied by any number of known techniques, including dipping, spraying, rolling, spin coating and any other technique wherein the receptive material layer can be applied generally uniformly over the entire test surface of the substrate. An advantage of the current invention is that it does not require contact of a printing surface (e.g., silicone stamp) to the substrate during the printing process. This eliminates any possibility of contamination from the print surface, as well as uneven application or inking of the binding agents due to pressure, contact, and/or surface energy variations possible when using a contact printing process. The invention also includes contact printing methods of applying the coating, as long as such methods are conducted in a manner to prevent inconsistent pattern transfer and contamination from contact during the initial coating process.

The receptive material is "tagged" or "labeled" with a radiation absorbing member (RAM) that will emit energy upon excitation thereof, generate reactive species, or a combination of these two. Thus, the RAM may be, for example, a fluorophore such as a fluorescent dye or fluorescent probe or a photoinitiator (photointitiator is defined here as a RAM capable of generating free radical species when irradiated with light at appropriate wavelength and amplitude.). The reactive species may be free radicals or thermally excited molecules. A molecule is said to be thermally excited when it undergoes a transition from an electronically excited state to its electronically ground state without emitting light. The energy that was originally stored in the electronically excited state molecules is transformed into a thermal energy making the molecules thermally excited.

The receptive material may be tagged with the RAM, for example, in a buffered solution wherein the RAM is covalently linked to biomolecules. The solution may subsequently be coated onto the substrate member in a light protected environment. Besides covalent bonding, other attachment techniques, such as adsorption, may be utilized. Alternatively, the receptive material and the RAM may be dissolved together and the solution of the mixture coated onto the substrate member in a light protected environment. Alternating layers of the RAM and the receptive material may also be used.

The receptive material layer is then defined into a pattern of active and inactive areas of receptive material by use of a mask having a pattern of protected or shielded areas and open or exposed areas. The mask is placed over the substrate in a light protected environment and the substrate and mask are subsequently irradiated with an electromagnetic radiation source at a wavelength and amplitude sufficient to excite the RAM through the open or exposed areas of the mask. Depending on the nature of RAM, the excited state form of the RAM will return to its ground state either by thermally dissipating the stored energy, or by emitting photons of energy, or both. Regardless of its exact nature, the emission can deactivate the surrounding receptors.

Alternatively, the excited RAM may undergo a photochemical degradation process that generates reactive species such as free radicals. The reactive species react with the receptive material in the immediate vicinity of the excited RAM and deactivate the receptors. Thus, the receptive material under the exposed areas of the mask is "deactivated" to the extent that it can no longer bind with conjugate ligands, including the analyte of interest. A pattern of active and inactive areas of receptive material is thus defined on the substrate.

The receptive material layer with attached Fluorescent RAM is irradiated with an energy source selected particularly for inducing fluorescence of the RAM without photobleaching the material. The energy source may be, for example, a light or laser source in the visible spectrum, such as a green or blue laser. The particular excitation source will be dependent on the characteristics of the RAM and biomolecules of the receptive material, the controlling factor being that the RAM not photo-bleach and emit sufficient energy to ultimately degrade the biomolecules. In some cases, it may be desirable to select the RAM such that its excitation wavelength is tuned to be particularly destructive to a specific region of the receptive material. One example may be in the case of an antibody as the receptive material, whereby a fluorophore is chosen to be tuned to the antigen-binding region of the antibody.

Upon subsequent exposure of the biosensor to a medium containing an analyte of interest, the analyte binds to the receptive material in the active areas. The biosensor will then diffract transmitted light thus creating a diffraction pattern. The diffraction pattern may be visible to the naked eye or, optionally, viewed or quantified with a sensing device.

By "diffraction" it is meant the phenomenon, observed when waves are obstructed by obstacles, of the disturbance spreading beyond the limits of the geometrical shadow of the object. The effect is marked when the size of the object is of similar order as the wavelength of the waves. In the present invention, the obstacles are analytes (with or without or attached microparticles) and the waves are light waves.

The present invention provides a low-cost, disposable biosensor which can be mass produced. The biosensors of the present invention can be produced as a single test for detecting an analyte or it can be formatted as a multiple test device. The uses for the biosensors of the present invention include, but are not limited to, detection of chemical or biological contamination in garments, such as diapers, the detection of contamination by microorganisms in prepacked foods such as fruit juices or other beverages, and the use of the biosensors of the present invention in health diagnostic applications such as diagnostic kits for the detection of antigens, microorganisms, and blood constituents. It should be appreciated that the present invention is not limited to any particular use or application.

These and other features and advantages of the present invention will become apparent after a review of the following detailed description of the disclosed embodiments.

DETAILED DESCRIPTION

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi and viruses. The biosensing devices according to the invention are relatively inexpensive and have advantages over conventional micro-contact printed biosensors.

The present invention comprises, in broad terms, a process of defining an active pattern of analyte-specific receptor material on a substrate surface by photo-masking the substrate. A generally uniform coating of RAM-tagged receptive material is applied to the substrate surface. A mask is placed over the substrate, and the mask and substrate combination is irradiated with an energy source. In its basic form, the "mask" serves to shield or "protect" at least one area or section of the receptive material from the irradiating energy source and to expose at least one adjacent section to the energy source. For example, the mask may be a generally transparent or translucent blank (e.g., a strip of material) having any pattern of shielded regions printed or otherwise defined thereon. The exposed unshielded regions of the mask correspond to the exposed areas of the substrate member. Alternatively, the mask may simply be a single object placed upon the substrate. The area under the object would be protected and thus define an active area of the receptive material, and the area around the object would be exposed to the energy source and thus define an area of inactive receptive material. Alternatively, the object may have any pattern of openings defined therethrough corresponding to the exposed areas.

If the RAM used as a label is a fluorophore, the energy source is particularly selected to induce fluorescence of the fluorophore exposed through the mask with minimal photobleaching of the material. Fluorescence is the result of a three-stage process that occurs in the fluorophores. In the first stage, energy is supplied by an external source, such as an incandescent lamp or a laser, and is absorbed by the fluorophore, creating an excited electronic singlet state. This process distinguishes fluorescence from chemiluminescence, in which the excited state is produced by a chemical reaction. In the second stage, the excited state exists for a finite time during which the fluorophore undergoes vibrational or conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorophore to its ground state. The emitted energy is lower than its excitation energy (light or laser), and thus of a longer wavelength. Photo-bleaching is the irreversible destruction of the excited fluorophore under high-intensity illumination conditions.

The emitted energy of the fluorophore material is ultimately transferred to the attached biomolecules and is sufficient to deactivate the biomolecules' previously function, be it catalytic or recognition (binding) by any one or combination of reactions that essentially destroys the bond structure of the biomolecules by a radical mechanism. For example, the transferred energy may result in sufficient heat to deactivate (or denature) and cause structural or functional hysteresis of the biomolecules. Alternatively, the transferred energy may cause free radicals that deactivate the biomolecules to be geneated. The result is that the receptive material exposed through the open/clear areas of the mask is rendered inactive. The receptive material under the shielded areas of the mask is protected during the irradiation step. Thus, upon removal of the mask, a pattern of active and inactive receptive material areas are defined. It should be understood that "pattern" includes as few as one active area and one inactive area. Upon subsequent exposure of the biosensor to a medium containing the analyte of interest, such analyte will bind to or react with the receptors in the active areas. The presence of the analyte or a surrogate thereof results in diffraction of transmitted and/or reflected light in a visible diffraction pattern corresponding to the active areas. As discussed in greater detail below, a diffraction enhancer may be used for enhancing diffraction from extremely small analytes.

The analytes that are contemplated as being detected using the present invention include, but are not limited to, bacteria; yeasts; fungi; viruses; rheumatoid factor; antibodies, including, but not limited to IgG, IgM, IgA, IgD, and IgE antibodies; carcinoembryonic antigen; streptococcus Group A antigen; viral antigens associated with autoimmune disease; PSA (prostate specific antigen) and CRP (C-reactive protein) antigens; allergens; tumor antigens; streptococcus Group B antigen; HIV I or HIV II antigen; or host response (antibodies) to these and other viruses; antigens specific to RSV or host response (antibodies) to the virus; antigen; enzyme; hormone; polysaccharide; protein; lipid; carbohydrate; drug or nucleic acid; *Salmonella* species; *Candida* species, including, but not limited to *Candida albicans* and *Candida tropicalis; Neisseria meningitides* groups A, B, C, Y and W sub 135, *Streptococcus pneumoniae; E. coli; Haemophilus influenza* type A/B; an antigen derived from microorganisms; a hapten; a drug of abuse; a therapeutic drug; an environmental agent; and antigens specific to *Hepatitis*. In broad terms, the "analyte of interest" may be thought of as any agent whose presence or absence from a biological sample is indicative of a particular health state or condition.

It is also contemplated that nutrients or receptors for a specific class of microorganism can be incorporated into the receptive material layer. In this way, very low concentrations of microorganisms can be detected by exposing the biosensor of the present invention with the nutrients incorporated therein to the suspect medium and then incubating the biosensor under conditions appropriate for the growth of the bound microorganism. The microorganisms are allowed to grow until there are enough organisms to form a diffraction pattern. Of course, in some cases, the microorganism is present or can multiply enough to form a diffraction pattern without the presence of a nutrient in the active receptive material areas.

The receptive material is characterized by an ability to specifically bind to or react with the analyte or analytes of interest. The variety of materials that can be used as receptive material is limited only by the types of material which will combine selectively (with respect to any chosen sample) with a secondary partner. Subclasses of materials which fall in the overall class of receptive materials include toxins, antibodies, antibody fragments, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, aptamers, peptides, and any other member of a specific binding pair. This list only incorporates some of the many different materials that can be coated onto the substrate surface to produce a thin film assay system. Whatever the selected analyte of interest is, the receptive material is designed to bind specifically with the analyte of interest.

As mentioned, the receptive material biomolecules are tagged with a RAM material. The use of RAM, such as fluorescent dyes and particles to tag or "label" biomolecular substances is widely known and understood by those skilled in the art. The RAM may be fluorescent molecules, polymers, dendrimers, particles, and the like. Some examples of suitable fluorescent molecules, for instance, include fluorescein, europium chelates, phycobiliprotein, rhodamine, and their derivative and analogs. Commercially available fluorescent dyes and particles (e.g. carboxylated microspheres) may be obtained from Molecular Probes, Inc. of Eugene, Oreg., USA. Some examples of suitable RAMs include, but are not limited to, monomethine dyes, trimethine dyes, pentamethine dyes, quinoline dyes, squaric acid-based dyes, and the like. Other examples of suitable dyes are described in U.S. Pat. Nos. 4,731,337 and 6,268,222, which are incorporated herein in their entirety by reference for all purposes. Applicants have found that a particularly well suited fluorescent dye is "Oregon Green 514" (activated with light at a wavelength of 514 nanometers) from Molecular Probes.

Binding of a fluorescent chromopohore to target biomolecules can dramatically affect the fluorescence yield of the chromophore and, with this realization in mind, the particular type of chromophore may be selected to increase the fluorescence yield. Fluorophores have been engineered to have a high fluorescence quantum yield when bound to a particular target biomolecule, but are otherwise effectively non-fluorescent. For example, Molecular Probes offers a line of "green" fluorescent dyes and probes that are particularly sensitive for biomolecular detection. This principle may also be exploited for the present invention. The fluorescence output of a given dye or other chromophore depends on the efficiency with which it absorbs and emits photons, and its ability to undergo repeated excitation/emission cycles without photo-bleaching. This "efficiency" is an important consideration under the principles of the present invention, because it is the repetition of this cycle that is relied on to "destroy" the attached biomolecules.

Attachment of the RAM to the receptive material biomolecules may be from a variety of well-known techniques. For instance, covalent attachment of RAM to the biomolecules can be accomplished with any number of functional groups, such as carboxylic, amino, aldehyde, bromoacetyl, iodoacetyl thiol, epoxy, and other reactive and linking functional groups through which a protein coupling reaction is accomplished. A surface functional group can also be incorporated as a functionalized co-monomer, particularly in the case of microparticle fluorophore probes which can contain a high surface concentration of the polar groups. In a particular embodiment, direct covalent linking with a protein is achieved by first activating the carboxylic groups of the RAM with carbodiimide. In an alternate embodient, a commercially available amine-reactive RAM, such as an N-hydroxysuccinimidyl ester, may be used. The activated carboxylic acid groups are reacted with an amino group of the biomolecules to form an amide bond. The activation and/or antibody coupling can occur in a buffer, such as a phosphate-buffered saline (PBS).

Besides covalent bonding, other attachment techniques, such as adsorption, may also be utilized in the present invention.

The matrix or medium containing the analyte of interest may be a liquid, a solid, or a gas, and can include a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material. For example, receptive material for bacteria may specifically bind a surface membrane component, protein or lipid, a polysaccharide, a nucleic acid, or an enzyme. The bacteria specific analyte may be a polysaccharide, an enzyme, a nucleic acid, a membrane component, or an antibody produced by the host in response to the bacteria. The presence or absence of the analyte may indicate an infectious disease (bacterial or viral), cancer or other metabolic disorder or condition. The presence or absence of the analyte may be an indication of food poisoning or other toxic exposure. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For immunoassays, an antibody may serve as the receptive material or it may be the analyte of interest. The receptive material, for example an antibody or an antigen, must form a stable, relatively dense, reactive layer on the substrate surface of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface or a decrease in the amount of receptive material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern becomes discernible in less than one hour after contact of the analyte with the biosensing device of the present invention.

The diffraction grating which produces the diffraction of light upon interaction with the analyte must have a minimum periodicity of about ½ the wavelength and a refractive index different from that of the surrounding medium. Very small analytes, such as viruses or molecules, can be detected indirectly by using a larger "diffraction-enhancing element," such as a micro-particle, that is specific for the small analyte. One embodiment in which the small analyte can be detected comprises coating the enhancing particle, such as a latex bead or polystyrene bead, with a receptive material, such as an antibody, that specifically binds to the analyte of interest. Particles that can be used in the present invention include, but are not limited to, glass, cellulose, synthetic polymers or plastics, latex, polystyrene, polycarbonate, proteins, bacterial or fungal cells, silica, cellulose acetate, carbon, and the like. The particles are desirably spherical in shape, but the structural and spatial configuration of the particles is not critical to the present invention. For instance, the particles could be slivers, ellipsoids, cubes, random shape and the like. A desirable particle size ranges from a diameter of approximately 0.1 micron to 50 microns, desirably between approximately 0.1 micron and 2.0 microns. The composition of the particle is not critical to the present invention.

Desirably, the receptive material layer on the substrate will specifically bind to an epitope on the analyte that is different from the epitope used in the binding to the enhancing particle. Thus, for detecting a small analyte, such as viral particles, in a medium, the medium is first exposed to the latex particles having the virus-specific receptive material thereon. The small analytes of interest in the medium will bind to the latex particles. Then, the latex particles are optionally washed and exposed to the biosensor film with the pattern of active receptive material areas containing the virus-specific antibodies. The antibodies then bind to the viral particles on the latex bead thereby immobilizing the latex beads in the same pattern as the active areas on the film. Because the bound latex beads will cause diffraction of the visible light, a diffraction pattern is formed, indicating the presence of the viral particle in the liquid. Other combinations using diffraction enhancing particles are described, for example, in U.S. Pat. No. 6,221,579 incorporated herein for all purposes.

Any one of a wide variety of materials may serve as the substrate to which the receptive material is applied. Such materials are well known to those skilled in the art. For example, the substrate may be formed of any one of a number of suitable plastics, metal coated plastics and glass, functionalized plastics and glass, silicon wafers, foils, glass, etc. Rather than requiring a rigid substrate for the photopatterning process described herein, it has been found that thermoplastic films are quite suitable. Such films include, but are not limited to, polymers such as: polyethyleneterephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene—vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80 percent. Other suitable thermoplastics and suppliers may be found, for example, in reference works such as the Modern Plastics Encyclopedia (McGraw-Hill Publishing Co., New York 1923–1996).

In one embodiment of the invention, the thermoplastic film may have a metal coating. The film with metal coating thereon may have an optical transparency of between approximately 5 percent and 95 percent. A more desired optical transparency for the thermoplastic film used in the present invention is between approximately 20 percent and 80 percent. In a desired embodiment of the present invention, the thermoplastic film has at least an approximately 80 percent optical transparency, and the thickness of the metal coating is such as to maintain an optical transparency greater than about 20 percent, so that diffraction patterns can be produced by either reflected or transmitted light. This corresponds to a metal coating thickness of about 20 nanometers. However, in other embodiments of the invention, the metal thickness may be between approximately 1 nanometer and 1000 nanometers.

The preferred metal for deposition on the film is gold. However, silver, aluminum, chromium, copper, iron, zirconium, platinum, titanium, and nickel, as well as oxides of these metals, may be used. Chromium oxide can be used to make metalized layers.

The RAM-tagged receptive material may be applied to the substrate by any conventional method. The material is applied so that it generally uniformly covers an entire (for example, upper) surface of the substrate. Non-contact methods for applying the receptive material may be desired so as to eliminate the possibility of contamination by contact during application. Suitable application methods include, but are not limited to, dipping, spraying, rolling, spin coating, and any other technique wherein the receptive material layer can be applied generally uniformly over the entire test surface of the substrate. Simple physisorption can occur on many materials, such as polystyrene, polycarbonates, glass, nylon, or other materials well known to those skilled in the art. One particular embodiment of immobilizing the analyte-specific receptive material layer involves molecular attachment, such as that possible between thiol or disulfide-containing compounds and gold. Typically, a gold coating of about 5 to about 2000 nanometers thick is supported on a silicon wafer, glass, or polymer film (such as a MYLAR® film). The analyte-specific receptor attaches to the gold surface upon exposure of a solution of the receptive material.

Although not preferred, the invention also includes contact printing methods of applying the coating. The technique selected should minimize the amount of receptive material required for coating a large number of test surfaces and maintain the stability/functionality of the receptive material during application without contamination. The technique should also apply or adhere the receptive material to the substrate in a uniform and reproducible fashion.

It is also contemplated that the receptive material layer may be formed on the substrate as a self-assembling monolayer of alkanethiolates, carboxylic acids, hydroxamic acids, and phosphonic acids on metalized thermoplastic films. The self-assembling monolayers have receptive material bound thereto. Reference is made to U.S. Pat. No. 5,922,550 for a more detailed description of such self-assembling monolayers and methods for producing the monolayers. The '550 patent is incorporated herein in its entirety for all purposes.

The mask may be formed of any suitable material that protects the underlying portion of the substrate from the irradiating energy source. A material that has proven useful for defining patterns of active and inactive receptive material regions on a gold-coated MYLAR® film coated with an antibody solution where the energy source is UV light is a transparent or translucent polymer film (such as MYLAR®) having a pattern of shielded or protected regions printed thereon. This type of mask is useful for light sources with a wavelength equal or greater than about 330 nanometers. For light sources having a wavelength below about 330 nanometers, a quartz or fused silica mask having chrome or other metal plated shielded regions defined thereon may be used. It may be desired to select a hole pattern and size so as to maximize the visible diffraction contrast between the active and inactive regions. It has been found suitable if the active regions are defined as generally circular with a diameter of about 10 microns and spaced from each other by about 5 microns.

Any suitable energy source may be selected for irradiating the mask and substrate combination to induce a change in the energy state of the RAM material. The energy source is selected for the particular absorption properties of the RAM, and has a wavelength and amplitude so as to either generate reactive species capable of deactivating the receptive material or induce repeated excitation/emission cycles without photo-bleaching of the RAM material. Light in the visible spectrum, e.g., a blue or green laser, is particularly well suited for the present invention. Care should be taken that the energy source does not damage (e.g., melt) the underlying substrate or mask.

Figure 1:
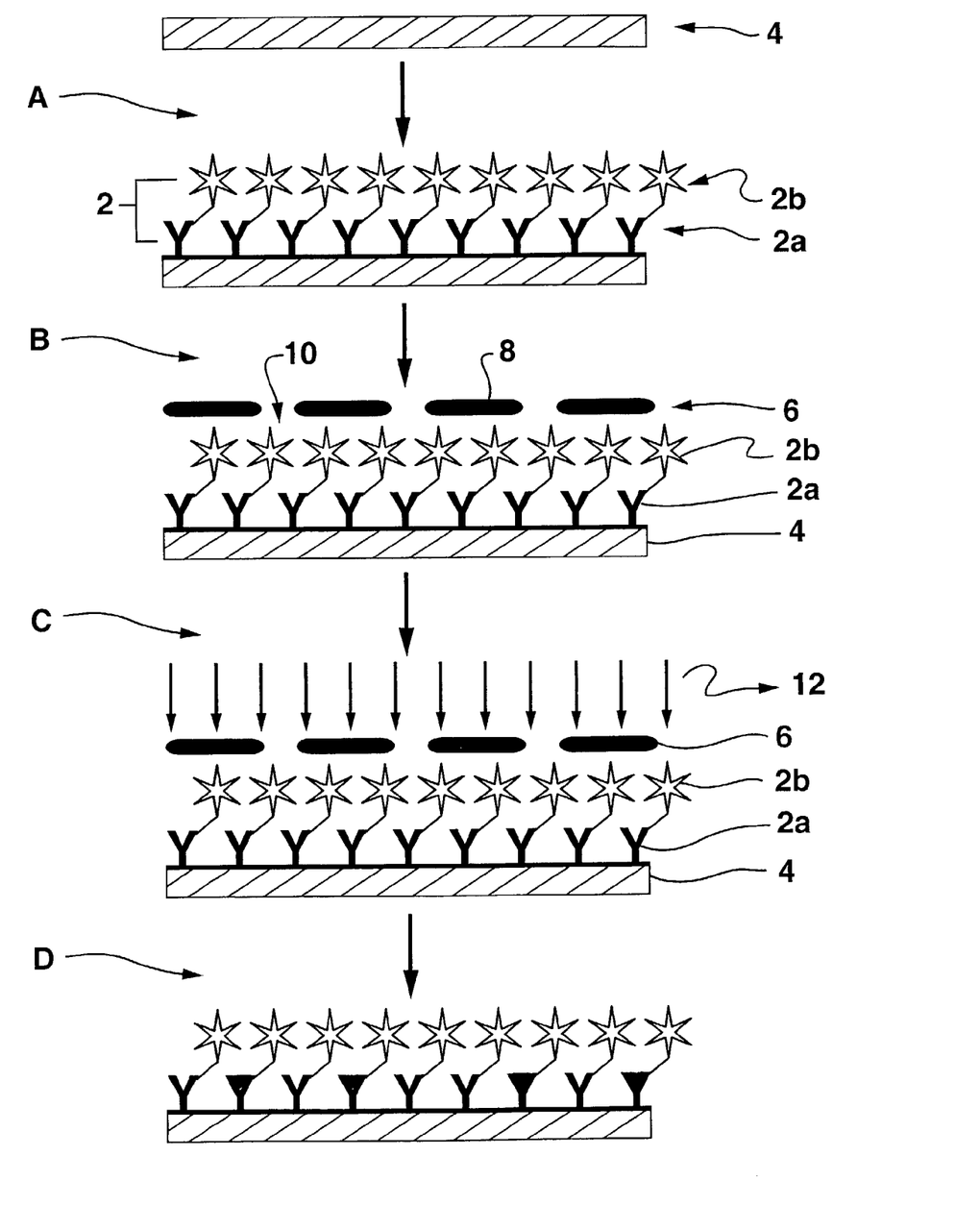
FIG. 1 is a schematic representation of a method for producing biosensors according to the invention by a masking process.

FIG. 1 is a schematic representation of one method for producing biosensors according to the invention. Step A represents the RAM tagged biomolecules applied (in a light protected environment) as a receptive material layer 2 to a substrate member 4. The biomolecules are represented as elements 2a, and the RAM tags are represented as elements 2b. Step B represents a mask 6 disposed over the substrate member 4. The mask 8 includes exposed or open regions 10 and shielded or protected regions 8 defined thereon. Step C represents the mask 6 and substrate member 4 combination being irradiated with a light source 12 to induce excitation of the RAM 2b under the exposed regions 10 of the mask 6. It can be seen that the fluorophores 2b underlying the shielded regions 8 of the mask 6 are shielded from the light source 12. The biomolecules 2a attached to the exposed RAM are rendered inactive from the energy transferred by the activated RAM 2b. Step D represents the biosensor after the mask 6 is removed. The biosensors are packaged and/or stored in a light protected environment until use and should have a relatively long shelf like if adequately shielded. The biosensor includes a pattern of active and inactive areas of biomolecules that corresponds to the pattern of the exposed 10 and shielded regions 8 of the mask 6.

In use, the biosensor is exposed in a light protected environment to a medium containing the analyte of interest.

The analyte will bind with the active receptive material biomolecules and, upon subsequent exposure of the biosensor to direct or reflected light, will produce a detectable diffraction pattern, as discussed above.

The biosensors according to the invention have a wide range of uses in any number of fields. The uses for the biosensors of the present invention include, but are not limited to, detection of chemical or biological contamination in garments, such as diapers, generally the detection of contamination by microorganisms in prepacked foods such as meats, fruit juices or other beverages, and the use of the biosensors of the present invention in health diagnostic applications such as diagnostic kits for the detection of proteins, hormones, antigens, DNA, microorganisms, and blood constituents. The present invention can also be used on contact lenses, eyeglasses, window panes, pharmaceutical vials, solvent containers, water bottles, band-aids, wipes, and the like to detect contamination. In one embodiment, the present invention is contemplated in a dipstick form in which the patterned substrate is mounted at the end of the dipstick. In use the dipstick is dipped into the liquid in which the suspected analyte may be present and allowed to remain for several minutes. The dipstick is then removed and then, either a light is projected through the substrate or the substrate is observed with a light reflected from the substrate. If a diffraction pattern is observed, then the analyte is present in the liquid.

In another embodiment of the present invention, a multiple analyte test is constructed on the same support. A strip may be provided with several patterned substrate sections. Each section has a different receptive material that is different for different analytes. It can be seen that the present invention can be formatted in any array with a variety of patterned substrates thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

What is claimed is:

1. A method of making a biosensor, comprising the steps of:
    forming a receptive material layer of biomolecules and a radiation-absorbing member generally uniformly over a surface of a substrate member in a light protected environment, the biomolecules being specific for an analyte of interest;
    placing a mask over the substrate member, the mask having a configuration so as to cover at least one underlying area of the substrate member while exposing at least one adjacent area;
    exposing the substrate member and mask combination with a radiation source sufficient to excite said radiation-absorbing member and, deactivate the biomolecules in the areas exposed by the mask;
    removing the mask from the substrate member; and
    wherein a resulting pattern of active and inactive areas of the receptive material are defined, the inactive areas corresponding to the areas exposed by the mask and the active areas corresponding to the areas underlying the mask such that when the biosensor is exposed to a medium containing the analyte of interest, the analyte binds to the receptive material in the active areas and subsequently facilitates diffraction of transmitted, reflected, or phase-shifted light in a diffraction pattern corresponding to the active areas.

2. The method as in claim 1, wherein the radiation absorbing member is a fluorophore.

3. The method as in claim 2, wherein said step of exposing with the radiation source includes illuminating the substrate member at a wavelength and amplitude sufficient for inducing fluorescence without photo-bleaching the fluorophore.

4. The method as in claim 1, wherein the radiation-absorbing member is a photoinitiator.

5. The method as in claim 4, wherein the step of exposing with the radiation source includes illuminating with a light at a wavelength and amplitude sufficient to generate free radicals sufficient to deactivate the biomolecules in the areas exposed by the mask.

6. The method as in claim 4, wherein the step of exposing with radiation source includes illuminating with a light at a wavelength and amplitude sufficient to generate thermally excited molecules sufficient to deactivate the biomolecules in the areas exposed by the mask.

7. The method as in claim 1, comprising selecting the substrate member from the group of materials consisting of plastics, metal coated plastics and glass, functionalized plastics and glass, silicon wafers, glass, and foils.

8. The method as in claim 7, wherein the substrate member is a metal coated plastic, and comprising selecting the metal from the group consisting of gold, silver, chromium, nickel, platinum, aluminum, iron, copper, titanium, gold oxide, chromium oxide, silver oxide, and zirconium.

9. The method as in claim 8, comprising depositing the gold coating onto the polymer film at a thickness between about 1 nanometer and 1000 nanometers.

10. The method as in claim 1, wherein the receptive material is a protein or proteins.

11. The method as in claim 10, wherein the receptive material is an antibody.

12. The method as in claim 1, comprising selecting the receptive material from at least one of antigens, antibodies, nucleotides, chelators, enzymes, bacteria, yeasts, fungi, viruses, bacterial pili, bacterial flagellar materials, nucleic acids, polysaccharides, lipids, proteins, carbohydrates, metals, hormones, aptamers, peptides, and respective receptors for said materials.

13. The method as in claim 1, wherein the analyte of interest is selected from at least one of a bacteria, yeast, fungus, virus, rheumatoid factor, IgG, IgM, IgA, IgD and IgE antibodies, carcinoembryonic antigen, streptococcus Group A antigen, viral antigens, antigens associated with autoimmune disease, allergens, tumor antigens, streptococcus group B antigen, HIV I or HIV II antigen, antibodies viruses, antigens specific to RSV, an antibody, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coli* K1, *Haemophilus influenza* type A/B, an antigen derived from microorganisms, PSA and CRP antigens, a hapten, a drug of abuse, a therapeutic drug, an environmental agents, or antigens specific to *Hepatitis*.

14. The method as in claim 1, further comprising defining a plurality of openings through the mask in a desired pattern, the openings defining the pattern of inactive areas.

* * * * *